United States Patent
Rinehart et al.

(10) Patent No.: US 9,648,908 B1
(45) Date of Patent: May 16, 2017

(54) E-VAPING DEVICE

(71) Applicant: Altria Client Services LLC, Richmond, VA (US)

(72) Inventors: Steve R. Rinehart, Chesterfield, VA (US); Barry S. Smith, Hopewell, VA (US); Charles Dendy, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 37 days.

(21) Appl. No.: 14/572,360

(22) Filed: Dec. 16, 2014

(51) Int. Cl.
 *A24F 47/00* (2006.01)
(52) U.S. Cl.
 CPC ............ *A24F 47/008* (2013.01); *A24F 47/00* (2013.01)
(58) Field of Classification Search
 CPC ...... A24F 47/00; A24F 47/002; A24F 47/004; A24F 47/008; A61M 15/06
 See application file for complete search history.

(56) References Cited

U.S. PATENT DOCUMENTS

| | | | |
|---|---|---|---|
| 5,595,706 A | 1/1997 | Sikka et al. | |
| 2013/0192623 A1 | 8/2013 | Tucker et al. | |
| 2015/0313275 A1* | 11/2015 | Anderson | A24B 15/10 131/352 |

OTHER PUBLICATIONS

Vapecore, Vaping 101:The Anatomy of an Evod—Vape Core (downloaded online from archive.org), Feb. 15, 2014 (downloaded on May 13, 2016).*

(Continued)

*Primary Examiner* — Anthony Calandra
(74) *Attorney, Agent, or Firm* — Harness, Dickey & Pierce, PLC

(57) ABSTRACT

An e-vaping device includes a first section capable of containing a liquid material. The first section includes a heater capable of vaporizing the liquid material, and a wick capable of drawing the liquid material to the heater. A male threaded connection with non-standard male threads is on one end of the first section. The e-vaping device also includes a second section with a power supply. The second section includes a female threaded connection on one end, where the female threaded connection includes female threads that mate with the non-standard male threads of the first section.

3 Claims, 17 Drawing Sheets

(56) References Cited

OTHER PUBLICATIONS

Maryland Metrics, Thread Data Charts(downloaded online from archive.org), Mar. 2012 (downloaded on May 15, 2016).*
www.e-cigarette-forum.com, Need to Identify threads on VaporX XLT battery, Dec. 2012 (downloaded on May 13, 2016).*
www.e-cigarette-forum.com, 510 Thread Size, Oct. 2012 (downloaded on May 13, 2016).*
Vaping Blog, .E-Cigarette battery threads, Oct. 3, 2013 [downloaded online Jan. 3, 2017 from ecigarettevapeshop.com].*
ISO Standard 68-1, "ISO general purpose screw threads—Basic profile—Metric screw threads," published in 1998, reviewed Apr. 11, 2014.
ISO 261, "ISO general purpose metric screw threads—General plan," published in 1998, reviewed Apr. 11, 2014.
ISO 262, "ISO general purpose metric screw threads—Selected sizes for screws, bolts and nuts," published in 1998, reviewed Apr. 11, 2014.
ISO 965-1, "Principles and basic data," published Sep. 13, 2013.
ISO 965-2, "Limits of sizes for general purpose external and internal screw threads," published in 1998, reviewed Apr. 11, 2014.
ISO 965-3, "Deviations for constructional screw threads," published in 1998, reviewed Apr. 11, 2014.
"The Mistic Bridge: PV Technology for Your E Cig," (from http://blog.misticecigs.com).

* cited by examiner

METRIC THREAD -- FINE PITCH -- M (1 mm - 28 mm)
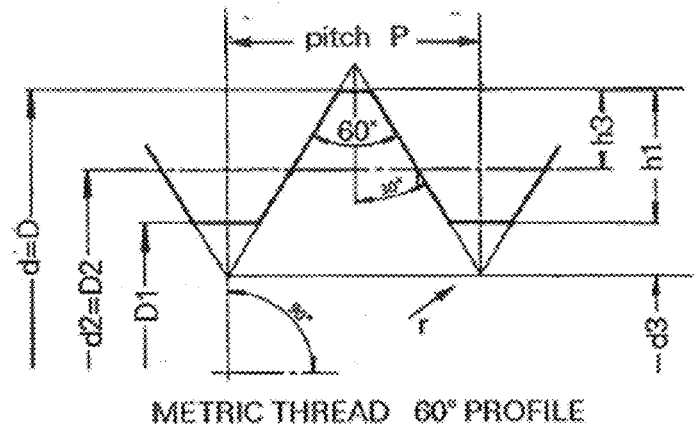
METRIC THREAD 60° PROFILE
FIG. 3A
(CONVENTIONAL)

FIG. 3E: Thread Data for Metric Thread with Fine Pitch

| Nominal Size ISO MF | Thread Form Type | Major Diam. mm d=D | Pitch mm P | Root Radius mm r | Pitch Diam. mm d2=D2 | Minor Diam. Male Thd. d3 | Minor Diam. Female Thd. D1 | Thread Height Male Thd. h3 | Thread Height Female Thd. H1 | Tap Drill Diam. mm |
|---|---|---|---|---|---|---|---|---|---|---|
| 1.0x0.2 | M | 1.00 | 0.20 | 0.029 | 0.870 | 0.755 | 0.783 | 0.123 | 0.108 | 0.80 |
| 1.1x0.2 | M | 1.10 | 0.20 | 0.029 | 0.970 | 0.855 | 0.883 | 0.123 | 0.108 | 0.90 |
| 1.2x0.2 | M | 1.20 | 0.20 | 0.029 | 1.070 | 0.955 | 0.983 | 0.123 | 0.108 | 1.00 |
| 1.4x0.2 | M | 1.40 | 0.20 | 0.029 | 1.270 | 1.155 | 1.183 | 0.123 | 0.108 | 1.20 |
| 1.6x0.2 | M | 1.60 | 0.20 | 0.029 | 1.470 | 1.355 | 1.383 | 0.123 | 0.108 | 1.40 |
| 1.8x0.2 | M | 1.80 | 0.20 | 0.029 | 1.670 | 1.555 | 1.583 | 0.123 | 0.108 | 1.60 |
| 2x0.25 | M | 2.00 | 0.25 | 0.036 | 1.838 | 1.693 | 1.729 | 0.153 | 0.135 | 1.75 |
| 2.2x0.25 | M | 2.20 | 0.25 | 0.036 | 2.038 | 1.893 | 1.929 | 0.153 | 0.135 | 1.95 |
| 2.5x0.35 | M | 2.50 | 0.35 | 0.051 | 2.273 | 2.071 | 2.121 | 0.215 | 0.189 | 2.10 |
| 3x0.35 | M | 3.00 | 0.35 | 0.051 | 2.773 | 2.571 | 2.621 | 0.215 | 0.189 | 2.60 |
| 3.5x0.35 | M | 3.50 | 0.35 | 0.051 | 3.273 | 3.071 | 3.121 | 0.215 | 0.189 | 3.10 |
| 4x0.5 | M | 4.00 | 0.50 | 0.072 | 3.675 | 3.387 | 3.459 | 0.307 | 0.271 | 3.50 |
| 4.5x0.5 | M | 4.50 | 0.50 | 0.072 | 4.175 | 3.887 | 3.959 | 0.307 | 0.271 | 4.00 |
| 5x0.5 | M | 5.00 | 0.50 | 0.072 | 4.675 | 4.387 | 4.459 | 0.307 | 0.271 | 4.50 |
| 5.5x0.5 | M | 5.50 | 0.50 | 0.072 | 5.175 | 4.887 | 4.959 | 0.307 | 0.271 | 5.00 |
| 6x0.75 | M | 6.00 | 0.75 | 0.108 | 5.513 | 5.080 | 5.188 | 0.460 | 0.406 | 5.20 |
| 7x0.75 | M | 7.00 | 0.75 | 0.108 | 6.513 | 6.080 | 6.188 | 0.460 | 0.406 | 6.20 |
| 8x0.75 | M | 8.00 | 0.75 | 0.108 | 7.513 | 7.080 | 7.188 | 0.460 | 0.406 | 7.20 |
| 8x1.0 | M | 8.00 | 1.00 | 0.144 | 7.350 | 6.773 | 6.917 | 0.613 | 0.541 | 7.00 |
| 9x0.75 | M | 9.00 | 0.75 | 0.108 | 8.513 | 8.080 | 8.188 | 0.460 | 0.406 | 8.20 |

FIG. 3F: Thread Data for Metric Thread with Fine Pitch

| Nominal Size ISO MF | Thread Form Type | Major Diam. mm d=D | Pitch mm P | Root Radius mm r | Pitch Diam. mm d2=D2 | Minor Diam. Male Thd. d3 | Minor Diam. Female Thd. D1 | Thread Height Male Thd. h3 | Thread Height Female Thd. H1 | Tap Drill Diam mm |
|---|---|---|---|---|---|---|---|---|---|---|
| 9x1 | M | 9.00 | 1.00 | 0.144 | 8.350 | 7.773 | 7.917 | 0.613 | 0.541 | 8.00 |
| 10x0.75 | M | 10.00 | 0.75 | 0.108 | 9.513 | 9.080 | 9.188 | 0.460 | 0.406 | 9.20 |
| 10x1 | M | 10.00 | 1.00 | 0.144 | 9.350 | 8.773 | 8.917 | 0.613 | 0.541 | 9.00 |
| 10x1.25 | M | 10.00 | 1.25 | 0.180 | 9.188 | 8.466 | 8.647 | 0.767 | 0.677 | 8.80 |
| 11x0.75 | M | 11.00 | 0.75 | 0.108 | 10.513 | 10.080 | 10.188 | 0.460 | 0.406 | 10.20 |
| 11x1 | M | 11.00 | 1.00 | 0.144 | 10.350 | 9.773 | 9.917 | 0.613 | 0.541 | 10.00 |
| 12x1 | M | 12.00 | 1.00 | 0.144 | 11.350 | 10.773 | 10.917 | 0.613 | 0.541 | 11.00 |
| 12x1.25 | M | 12.00 | 1.25 | 0.180 | 11.188 | 10.466 | 10.647 | 0.767 | 0.677 | 10.80 |
| 12x1.5 | M | 12.00 | 1.50 | 0.217 | 11.026 | 10.160 | 10.376 | 0.920 | 0.812 | 10.50 |
| 14x1.0 | M | 14.00 | 1.00 | 0.144 | 13.350 | 12.773 | 12.917 | 0.613 | 0.541 | 13.00 |
| 14x1.25 | M | 14.00 | 1.25 | 0.180 | 13.188 | 12.466 | 12.647 | 0.767 | 0.677 | 12.80 |
| 14x1.5 | M | 14.00 | 1.50 | 0.217 | 13.026 | 12.160 | 12.376 | 0.920 | 0.812 | 12.50 |
| 15x1 | M | 15.00 | 1.00 | 0.144 | 14.350 | 13.773 | 13.917 | 0.613 | 0.541 | 14.00 |
| 15x1.5 | M | 15.00 | 1.50 | 0.217 | 14.026 | 13.160 | 13.376 | 0.920 | 0.812 | 13.50 |
| 16x1 | M | 16.00 | 1.00 | 0.144 | 15.350 | 14.773 | 14.917 | 0.613 | 0.541 | 15.00 |
| 16x1.5 | M | 16.00 | 1.50 | 0.217 | 15.026 | 14.160 | 14.376 | 0.920 | 0.812 | 14.50 |
| 17x1.0 | M | 17.00 | 1.00 | 0.144 | 16.350 | 15.773 | 15.917 | 0.613 | 0.541 | 16.00 |
| 17x1.5 | M | 17.00 | 1.50 | 0.217 | 16.026 | 15.160 | 15.376 | 0.920 | 0.812 | 15.50 |
| 18x1.0 | M | 18.00 | 1.00 | 0.144 | 17.350 | 15.773 | 19.917 | 0.613 | 0.541 | 17.00 |
| 18x1.5 | M | 18.00 | 1.50 | 0.217 | 17.026 | 16.160 | 16.376 | 0.920 | 0.812 | 16.50 |
| 18x2.0 | M | 18.00 | 2.00 | 0.289 | 16.701 | 15.546 | 15.835 | 1.227 | 1.083 | 16.00 |
| 20x1.0 | M | 20.00 | 1.00 | 0.144 | 19.350 | 18.773 | 18.917 | 0.613 | 0.541 | 19.00 |

FIG. 3G: Thread Data for Metric Thread with Fine Pitch

| Nominal Size ISO MF | Thread Form Type | Major Diam. mm d=D | Pitch mm P | Root Radius mm r | Pitch Diam. mm d2=D2 | Minor Diam. Male Thd. d3 | Minor Diam. Female Thd. D1 | Thread Height Male Thd. h3 | Thread Height Female Thd. H1 | Tap Drill Diam. mm |
|---|---|---|---|---|---|---|---|---|---|---|
| 20x1.5 | M | 20.00 | 1.50 | 0.217 | 19.026 | 18.160 | 18.376 | 0.920 | 0.812 | 18.50 |
| 20x2.0 | M | 20.00 | 2.00 | 0.289 | 18.701 | 17.546 | 17.835 | 1.227 | 1.083 | 18.00 |
| 22x1.0 | M | 22.00 | 1.00 | 0.144 | 21.350 | 20.773 | 20.917 | 0.613 | 0.541 | 21.00 |
| 22x1.5 | M | 22.00 | 1.50 | 0.217 | 21.026 | 20.160 | 20.376 | 0.920 | 0.812 | 20.50 |
| 22x2.0 | M | 22.00 | 2.00 | 0.289 | 20.701 | 19.546 | 19.835 | 1.227 | 1.083 | 20.00 |
| 24x1.0 | M | 24.00 | 1.00 | 0.144 | 23.350 | 22.773 | 22.917 | 0.613 | 0.541 | 23.00 |
| 24x1.5 | M | 24.00 | 1.50 | 0.217 | 23.026 | 22.160 | 22.376 | 0.920 | 0.812 | 22.50 |
| 24x2.0 | M | 24.00 | 2.00 | 0.289 | 22.701 | 21.546 | 21.835 | 1.227 | 1.083 | 22.00 |
| 25x1.0 | M | 25.00 | 1.00 | 0.144 | 24.350 | 23.773 | 23.917 | 0.613 | 0.541 | 24.00 |
| 25x1.5 | M | 25.00 | 1.50 | 0.217 | 24.026 | 23.160 | 23.376 | 0.920 | 0.812 | 23.50 |
| 25x2.0 | M | 25.00 | 2.00 | 0.289 | 23.701 | 22.546 | 22.835 | 1.227 | 1.083 | 23.00 |
| 27x1.0 | M | 27.00 | 1.00 | .0144 | 26.350 | 25.773 | 25.917 | 0.613 | 0.541 | 26.00 |
| 27x1.5 | M | 27.00 | 1.50 | 0.217 | 26.026 | 25.160 | 25.376 | 0.920 | 0.812 | 25.50 |
| 27x2.0 | M | 27.00 | 2.00 | 0.289 | 25.701 | 24.546 | 24.835 | 1.227 | 1.083 | 25.00 |
| 28x1.0 | M | 28.00 | 1.00 | 0.144 | 27.350 | 26.773 | 26.917 | 0.613 | 0.541 | 27.00 |
| 28x1.5 | M | 28.00 | 1.50 | 0.217 | 27.026 | 26.160 | 26.376 | 0.920 | 0.812 | 26.50 |
| 28x2.0 | M | 28.00 | 2.00 | 0.289 | 26.701 | 25.546 | 25.835 | 1.227 | 1.083 | 26.00 |

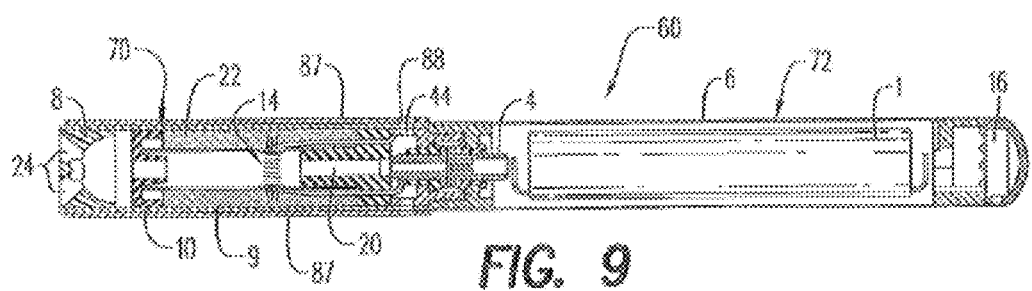
FIG. 9
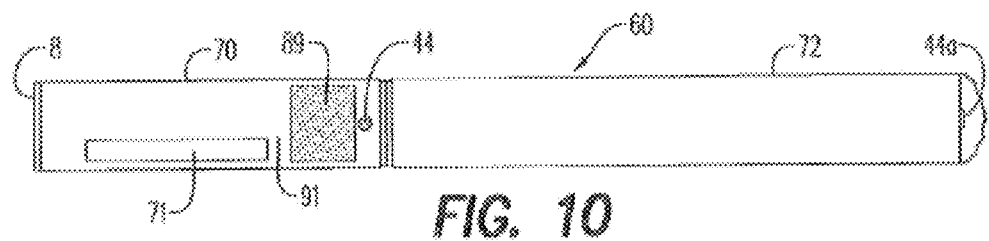
FIG. 10
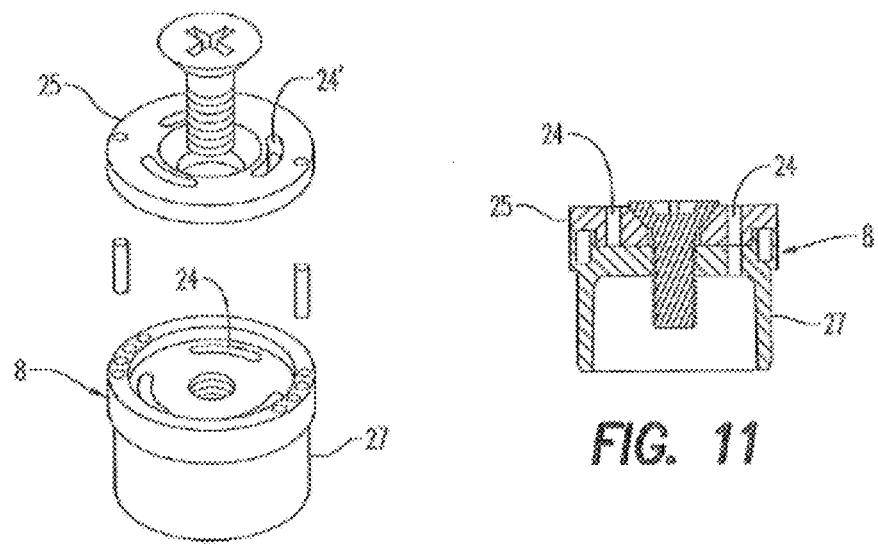
FIG. 11
FIG. 12

E-VAPING DEVICE

BACKGROUND OF THE INVENTION

Field of the Invention

Example embodiments relate generally to an e-vaping device.

Related Art

Electronic vaping devices are used to vaporize a liquid material into an aerosol or "vapor" in order for an adult vaper to inhale the vapor. These electronic vaping devices may be referred to as e-vaping devices. E-vaping devices include a heater which vaporizes liquid material to produce an aerosol. An e-vaping device may include several e-vaping elements including a power source, a cartridge or e-vaping tank including the heater and along with a reservoir capable of holding the liquid material.

SUMMARY OF THE INVENTION

At least one example embodiment relates to an e-vaping device.

In one example embodiment, the e-vaping includes a first section. The first section includes an outer cylindrical tube extending in a longitudinal direction, an inner cylindrical tube within the outer cylindrical tube, and a liquid supply comprising a liquid material. The liquid supply is contained in an outer annulus between the outer cylindrical tube and the inner cylindrical tube. The first section further includes a heater located in the inner cylindrical tube, a wick in communication with the liquid supply and in communication with the heater, a mouth piece in fluid communication the inner cylindrical tube at a proximal end of the first section, and a male threaded connector at a distal end of the first section. The male threaded connector has first threads with a non-standard pitch. The e-vapor device further includes a second section. The second section includes a power supply, and a female threaded connector at a proximal end of the second section. The female threaded connector has second threads mating with the non-standard pitch of the first threads.

In one embodiment, the dimensions of the first and second threads meet international standards organization (ISO) Standard Number 49:1994, with the exception of the non-standard pitch of the first and second threads.

In one embodiment, a major diameter of the male and female threads is 7.00 mm and the non-standard pitch of the first and second threads is 0.6 mm.

In one embodiment, the first threads have a root radius of 0.108 mm, a pitch diameter of 6.513 mm, a minor diameter of 6.080 mm, a thread height of 0.460 mm, and a tap drill diameter of 6.20 mm.

In one embodiment, the second threads have a root radius of 0.108 mm, a pitch diameter of 6.513 mm, a minor diameter of 6.188 mm, a thread height of 0.406 mm, and a tap drill diameter of 6.20 mm.

In another example embodiment, the e-vapor device includes a section. The section includes an outer cylindrical tube extending in a longitudinal direction, an inner cylindrical tube within the outer cylindrical tube, and a liquid supply including a liquid material. The liquid supply is contained in an outer annulus between the outer cylindrical tube and the inner cylindrical tube. The section further includes a heater located in the inner cylindrical tube, a wick in communication with the liquid supply and in communication with the heater, a mouth piece in fluid communication the inner cylindrical tube at a proximal end of the section, and a male threaded connector at a distal end of the section. The male threaded connector has threads with a non-standard pitch.

In one embodiment, the dimensions of the threads meet international standards organization (ISO) Standard Number 49:1994, with the exception of the non-standard pitch of the threads.

In one embodiment, a major diameter of the threads is 7.00 mm and the non-standard pitch of the threads is 0.6 mm.

In one embodiment, the threads have a root radius of 0.108 mm, a pitch diameter of 6.513 mm, a minor diameter of 6.080 mm, a thread height of 0.460 mm, and a tap drill diameter of 6.20 mm.

In another example embodiment, as e-vapor device includes a first section. The first section includes an outer cylindrical tube extending in a longitudinal direction, an inner cylindrical tube within the outer cylindrical tube, and a liquid supply including a liquid material. The liquid supply is contained in an outer annulus between the outer cylindrical tube and the inner cylindrical tube. The first section further includes a heater located in the inner cylindrical tube, a wick in communication with the liquid supply and in communication with the heater, a mouth piece in fluid communication the inner cylindrical tube at a proximal end of the first section, and a male threaded connector at a distal end of the first section. The male threaded connector has first threads with a proprietary pitch. The e-vapor device further includes a second section. The second section includes a power supply, and a female threaded connector at a proximal end of the second section. The female threaded connector has second threads mating with the proprietary pitch of the first threads.

In one embodiment, the dimensions of the first and second threads meet international standards organization (ISO) Standard Number 49:1994, with the exception of the proprietary pitch of the first and second threads.

In one embodiment, a major diameter of the male and female threads is 7.00 mm and the proprietary pitch of the first and second threads is 0.6 mm.

In one embodiment, the first threads have a root radius of 0.108 mm, a pitch diameter of 6.513 mm, a minor diameter of 6.080 mm, a thread height of 0.460 mm, and a tap drill diameter of 6.20 mm.

In one embodiment, the second threads have a root radius of 0.108 mm, a pitch diameter of 6.513 mm, a minor diameter of 6.188 mm, a thread height of 0.406 mm, and a tap drill diameter of 6.20 mm.

In another example embodiment, the e-vapor device includes a section. The section includes an outer cylindrical tube extending in a longitudinal direction, an inner cylindrical tube within the outer cylindrical tube, and a liquid supply including a liquid material. The liquid supply is contained in an outer annulus between the outer cylindrical tube and the inner cylindrical tube. The first section further includes a heater located in the inner cylindrical tube, a wick in communication with the liquid supply and in communication with the heater, a mouth piece in fluid communication the inner cylindrical tube at a proximal end of the section, and a male threaded connector at a distal end of the section. The male threaded connector has threads with a proprietary pitch.

In one embodiment, the dimensions of the threads meet international standards organization (ISO) Standard Number 49:1994, with the exception of the proprietary pitch of the threads.

In one embodiment, a major diameter of the threads is 7.00 mm and the proprietary pitch of the threads is 0.6 mm.

In one embodiment, the threads have a root radius of 0.108 mm, a pitch diameter of 6.513 mm, a minor diameter of 6.080 mm, a thread height of 0.460 mm, and a tap drill diameter of 6.20 mm.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 3A is a conventional diagram of a standard thread profile for international standards of organization (ISO) standard nominal sized threaded connections;

FIGS. 3E-3G list tabulated data corresponding to the dimensions of the ISO standard nominal sized threaded connections shown in FIG. 3A;

FIG. 9 is a cross-sectional view of an e-vaping device according to the first embodiment and further including a sleeve assembly, in accordance with an example embodiment;

FIG. 10 is a top view of an e-vaping device including an aroma strip on an outer surface thereof, in accordance with an example embodiment;

FIG. 11 is a cross-sectional view of a second embodiment of a mouth end insert for use with the e-vaping device of FIGS. 1, 4, 6 and 8, in accordance with an example embodiment;

FIG. 12 is an exploded view of the mouth end insert of FIG. 11, in accordance with an example embodiment.

DETAILED DESCRIPTION

Figures 1, 2A, 2B:
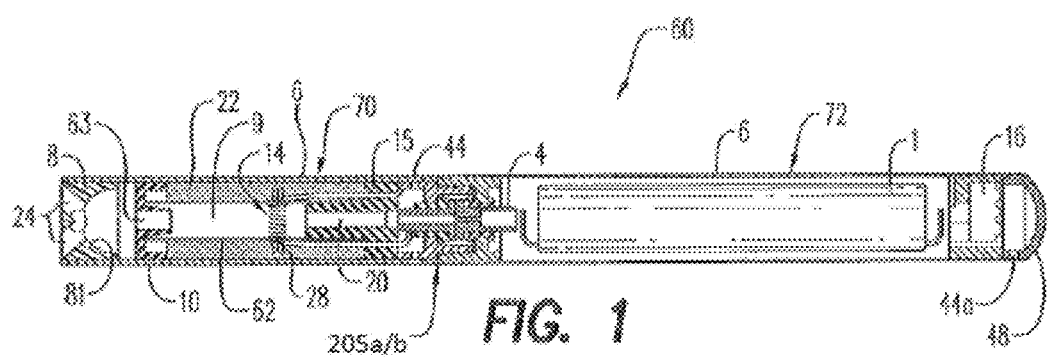
FIG. 1 is a cross-sectional view of an e-vaping device according to a first embodiment wherein the mouth end insert includes diverging outlets, in accordance with an example embodiment.
FIG. 2A is a perspective view of a mouth end insert for use with the e-vaping device of FIG. 1, in accordance with an example embodiment.
FIG. 2B is a cross-sectional view along line B-B of the mouth end insert of FIG. 2A, in accordance with an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As shown in FIGS. 1, 4, 6, 8, 9 and 13, a novel e-vaping device 60 comprises a replaceable cartridge (or first section) 70 and a reusable fixture (or second section) 72, which are coupled together at a threaded connection 205a/b (where 205a is a male threaded connection on cartridge 70, and 205b is a female threaded connection on reusable fixture 72) or by other convenience such as a snug-fit, detent, clamp and/or clasp. The first section 70 includes an outer tube 6 (or casing) extending in a longitudinal direction and an inner tube 62 coaxially positioned within the outer tube or casing 6. The second section 72 can also include an outer tube 6 (or casing) extending in a longitudinal direction. In an alternative embodiment, the outer tube 6 can be a single tube housing both the first section 70 and the second section 72 and the entire e-vaping device 60 can be disposable.

FIG. 3A is a diagram of a conventional, well-known standard thread profile for international standards of organization (ISO) standard for 1 mm-28 mm nominal sized connections. The diagram of FIG. 3A matches the tabulated data shown in FIG. 3E. The diagram of FIG. 3A and the tabulated data of FIG. 3E is commensurate with the following well-known ISO standards: ISO Standard 68-1, "ISO general purpose screw threads—Basic profile—Metric screw threads," published in 1998, reviewed Apr. 11, 2014 (referred to as "ISO 68-1:1998," throughout the remainder of this document); ISO 261, "ISO general purpose metric screw threads—General plan," published in 1998, reviewed Apr. 11, 2014; ISO 262, "ISO general purpose metric screw threads—Selected sizes for screws, bolts and nuts," published in 1998, reviewed Apr. 11, 2014; ISO 965-1, "Principles and basic data," published Sep. 13, 2013; ISO 965-2, "Limits of sizes for general purpose external and internal screw threads," published in 1998, reviewed Apr. 11, 2014; and ISO 965-3, "Deviations for constructional screw threads," published in 1998, reviewed Apr. 11, 2014. Each of these ISO standards is hereby incorporated by reference in their entirety.

Figure 3B:
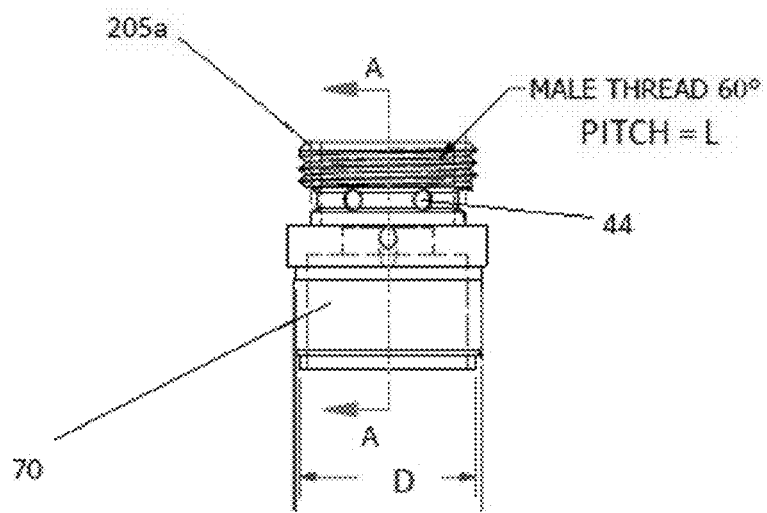
FIG. 3B is a side-view of a non-standard male threaded connection, in accordance with an example embodiment.

FIG. 3B is a side-view of a non-standard male threaded connection 205a, in accordance with an example embodiment. This non-standard male threaded connection 205a may be attached to and form part of cartridge 70. The male threaded connection 205a may be "non-standard," at least from the standpoint that the threaded connection may deviate from the well-known ISO standard threaded connection information included in FIG. 3A and Table 1. Specifically, in one embodiment, the pitch of the threaded male connection may deviate from the ISO standard. More specifically, the pitch may be smaller than the pitch indicated in the ISO standard information, such that the threaded connection has a higher thread count per linear distance of the thread. Most specifically, in one embodiment, for a male threaded connection with a major diameter (D) of 7 mm, the male threaded connection may have a root radius of 0.108 mm, a pitch diameter of 6.513 mm, a minor diameter of 6.080 mm, a thread height of 0.460 mm, a tap drill diameter of 6.20 mm, and pitch (L) may be a non-standard pitch length of 0.6 mm (which deviates from the standard pitch of 0.75 mm for a threaded connection with a major diameter of 7.00 mm, as shown in FIG. 3E).

Figure 3C:
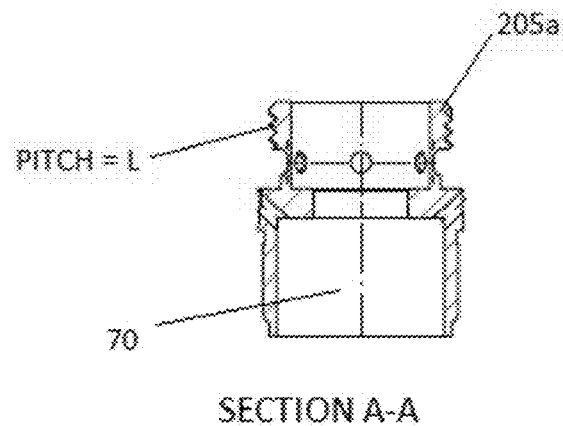
FIG. 3C is a cross-sectional view of the non-standard male threaded connection of FIG. 3B, in accordance with an example embodiment.

FIG. 3C is a cross-sectional view (from vantage point A-A) of the non-standard male threaded connection 205a of FIG. 3B, in accordance with an example embodiment. FIG. 3C more clearly highlights the 0.6 mm pitch of the 7 mm major diameter non-standard male threads.

Figure 3D:
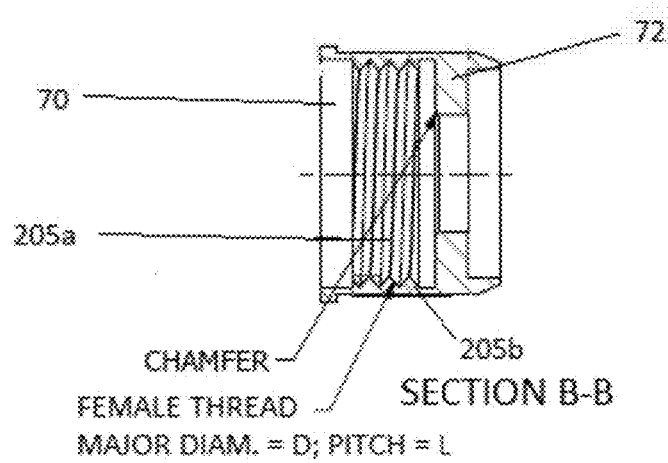
FIG. 3D is a cross-sectional view of a non-standard female threaded connection engaged with a non-standard male threaded connection, in accordance with an example embodiment.

FIG. 3D is a cross-sectional view of a non-standard female threaded connection 205b engaged with a non-standard male threaded connection 205a, in accordance with an example embodiment. In one embodiment, the female male threaded connection 205b may be "non-standard," at least from the standpoint that the threaded connection may deviate from the well-known ISO standard threaded connection information included in FIG. 3A and Table 1. Specifically, in one embodiment, the pitch of the threaded female connection 205b may deviate from the ISO standard. More specifically, in one embodiment, the pitch may be smaller than the pitch indicated in the ISO standard information, such that the threaded connection 205b has a higher thread count per linear distance of the thread. Most specifically, in one embodiment, for a female threaded connection 205b with a major diameter of 7 mm, the female threaded connection may have a root radius of 0.108 mm, a pitch diameter of 6.513 mm, a minor diameter of 6.188 mm, a thread height of 0.406 mm, a tap drill diameter of 6.20 mm, and pitch (L) may be a non-standard pitch length of 0.6 mm (which deviates from the standard pitch of 0.75 mm for a threaded connection with a major diameter of 7.00 mm, as shown in FIG. 3E). By using the non-standard female threaded connection 205b, the reusable fixture 72 may mate with any of a cartridge 70 that may be outfitted with non-standard male threaded connection 205a.

By providing the cartridge 70 with a non-standard male pitch, which is smaller than the standard pitch, the cartridge 70 may only be capable of correctly being connected to a female threaded connection with a corresponding same non-standard female pitch (for example, see the non-standard female threaded connection 205b for the reusable fixture 72 which may contain the battery 1, shown in FIG. 3D). By providing mating e-vaping elements with respective male and female threaded connections 205a/b a proprietary or unique threaded connections 205a/b is provided. This proprietary threading arrangement offers more precise engagement, and these connections 205a/b will more readily align with each other, as compared to standard threaded connections. Use of the proprietary threaded connections 205a/b will cause "binding" if attempts are made to mate a standard threaded connection to these non-standard connections 205a/b. When the binding occurs, any e-vaping component with a standard connection may not be capable of fully and correctly engaging with the cartridge 70. These non-standard threaded connections 205a/b may ensure that only e-vaping components with matching proprietary threaded connections may be mated to the connections, and therefore the non-standard threaded connections 205a/b may ensure a high quality product and an adult vaper experience in that only properly rated and authorized e-vaping elements may be used in conjunction with each other.

Referring again to FIG. 1, the e-vaping device 60 can also include a central air passage 20 defined in part by inner tube 62 and an upstream seal 15. Moreover, the e-vaping device 60 includes a liquid supply reservoir 22. The liquid supply comprises a liquid material and optionally a liquid storage medium 21 operable to store the liquid material therein. In an embodiment, the liquid supply reservoir 22 is contained in an outer annulus between the outer tube 6 and the inner tube 62. The annulus is sealed at an upstream end by the seal 15 and by a liquid stopper 10 at a downstream end so as to prevent leakage of the liquid material from the liquid supply reservoir 22.

In an embodiment, a heater 14 is also contained in the inner tube 62 downstream of and in spaced apart relation to the portion of central air passage 20 defined by the seal 15. The heater 14 can be in the form of a wire coil, a planar body, a ceramic body, a single wire, a cage of resistive wire or any other suitable form. A wick 28 is in communication with the liquid material in the liquid supply reservoir 22 and in communication with the heater 14 such that the wick 28 disposes liquid material in proximate relation to the heater 14. The wick 28 may be constructed of a fibrous and flexible material. The wick 28 may include at least one filament having a capacity to draw a liquid. For example, the wick 28 may comprise a bundle of filaments which may include glass (or ceramic) filaments. In another embodiment, a bundle comprising a group of windings of glass filaments, for example, three of such windings, all which arrangements are capable of drawing liquid via capillary action via interstitial spacing between the filaments. A power supply 1 in the second section 72 is may be operably connected to the heater 14 (as described below) to apply voltage across the heater 14. The e-vaping device 60 also includes at least one air inlet 44 operable to deliver air to the central air passage 20 and/or other portions of the inner tube 62.

Figure 7:
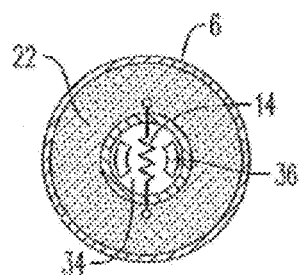
FIG. 7 is a cross-sectional view along line A-A of the e-vaping of FIG. 6, in accordance with an example embodiment.
Figure 8:
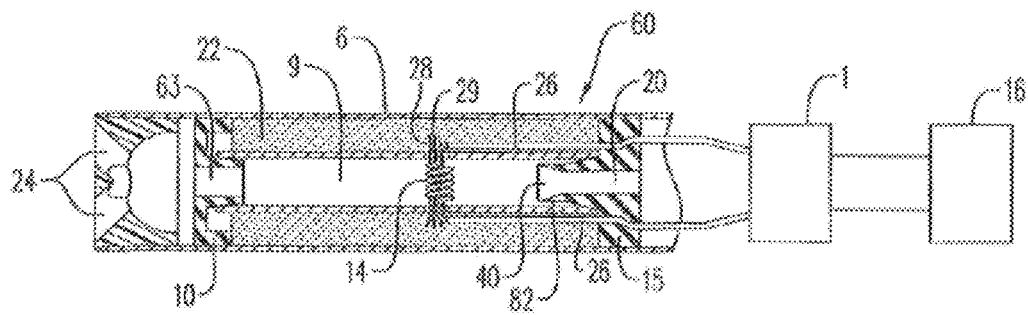
FIG. 8 is a cross-sectional view of an embodiment wherein an e-vaping device includes an air flow diverter, in accordance with an example embodiment.
Figure 13:
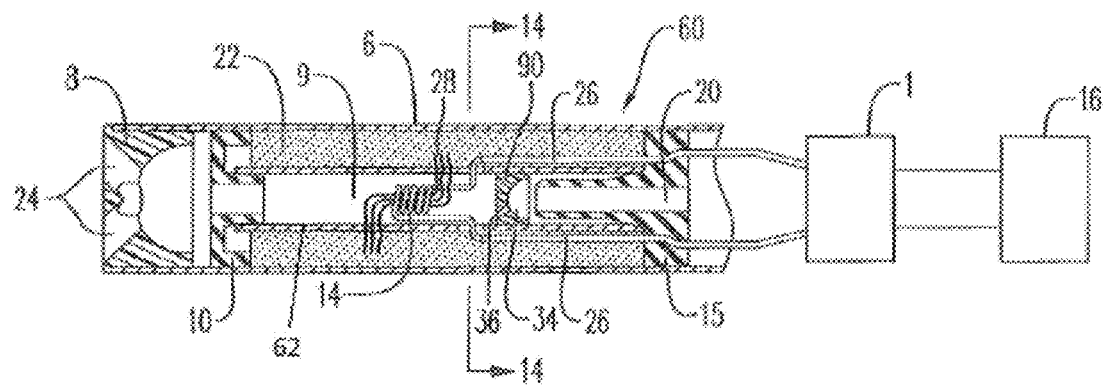
FIG. 13 is a cross-sectional view of an embodiment wherein an e-vaping device includes an air flow diverter, in accordance with an example embodiment.
Figure 14:
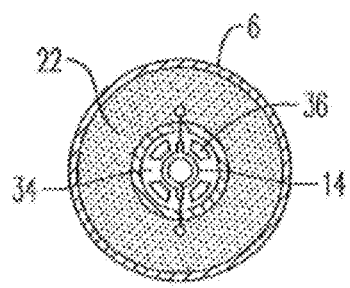
FIG. 14 is a cross-sectional view along line A'-A' of the e-vaping device of FIG. 13, in accordance with an example embodiment.

The e-vaping device 60 further includes a mouth end insert 8 having at least two off-axis, diverging outlets 24. The mouth end insert 8 is in fluid communication with the central air passage 20 via the interior of inner tube 62 and a central passage 63, which extends through the stopper 10. Moreover, as shown in FIGS. 7 and 8, the heater 14 extends in a direction transverse to the longitudinal direction and heats the liquid material to a temperature sufficient to vaporize the liquid material and form an aerosol. In other embodiments, other orientations of the heater 14 are contemplated. For example, as shown in FIG. 13, the heater 14 and the heated portion of the wick 28 can be arranged longitudinally within the inner tube 62. As shown, the heater 14 is arranged centrally within the inner tube 62. However, in other embodiments the heater 14 can be arranged adjacent an inner surface of the inner tube 62.

Referring now to FIG. 1, the wick 28, liquid supply reservoir 22 and mouth end insert 8 are contained in the cartridge 70 and the power supply 1 is contained in the second section 72. In one embodiment, the first section (the cartridge) 70 is disposable and the second section (the fixture) 72 is reusable. The sections 70, 72 can be attached by a threaded connection 205, as described above, whereby the downstream section 70 can be replaced when the liquid supply reservoir 22 is used up. Having a separate first section 70 and second section 72 provides a number of advantages. First, if the first section 70 contains the at least one heater 14, the liquid supply reservoir 22 and the wick 14, all elements which are potentially in contact with the liquid are disposed of when the first section 70 is replaced. Thus, there will be no cross-contamination between different mouth end inserts 8, for example, when using different liquid materials. Also, if the first section 70 is replaced at suitable intervals, there is little chance of the heater becoming clogged with liquid. Optionally, the first section 70 and the second section 72 are arranged to releasably lock together when engaged.

In one embodiment, as shown in FIG. 10, the outer tube 6 can include a clear (transparent) window 71 formed of a transparent material so as to allow an adult vaper to see the amount of liquid material remaining in the liquid supply reservoir 22. The clear window 71 can extend at least a portion of the length of the first section 70 and can extend fully or partially about the circumference of the first section 70. In another embodiment, the outer tube 6 can be at least partially formed of a transparent material so as to allow an adult vaper to see the amount of liquid material remaining in the liquid supply reservoir 22.

In an embodiment, the at least one air inlet 44 includes one or two air inlets 44, 44'. Alternatively, there may be three, four, five or more air inlets. If there is more than one air inlet 44, 44', the air inlets 44, 44' are located at different locations along the e-vaping device 60. For example, as shown in FIG. 1, an air inlet 44a can be positioned at the upstream end of the e-vaping device adjacent a puff sensor 16 such that the puff sensor 16 supplies power to the heater 14 upon sensing a puff by the adult vaper. Air inlet 44a should communicate with the mouth end insert 8 so that a draw upon the mouth end insert activates the puff sensor 16. The air from the air inlet 44a can then flow along the battery and to the central air passage 20 in the seal 15 and/or to other portions of the inner tube 62 and/or outer tube 6. At least one additional air inlet 44, 44' can be located adjacent and upstream of the seal 15 or at any other desirable location. Altering the size and number of air inlets 44, 44' can also aid in establishing the resistance to draw of the e-vaping device 60.

In an embodiment, the heater 14 is arranged to communicate with the wick 28 and to heat the liquid material contained in the wick 28 to a temperature sufficient to vaporize the liquid material and form an aerosol.

The heater 14 may be a wire coil surrounding wick 28. Examples of suitable electrically resistive materials include titanium, zirconium, tantalum and metals from the platinum group. Examples of suitable metal alloys include stainless steel, nickel-, cobalt-, chromium-, aluminium- titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 14 comprises at least one material selected from the group consisting of stainless steel, copper, copper alloys, nickel-chromium alloys, superalloys and combinations thereof. In an embodiment, the heater 14 is formed of nickel-chromium alloys or iron-chromium alloys. In one embodiment, the heater 14 can be a ceramic heater having an electrically resistive layer on an outside surface thereof.

In another embodiment, the heater 14 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al). Use of iron-aluminides is particularly advantageous in that they exhibit high resistivity. FeAl exhibits a resistivity of approximately 180 micro-ohms, whereas stainless steel exhibits approximately 50 to 91 micro-ohms. The higher resistivity lowers current draw or load on the power source (battery) 1.

In one embodiment, the heater 14 comprises a wire coil which at least partially surrounds the wick 28. In that embodiment, the wire may be a metal wire and/or the heater coil that extends partially along the length of the wick 28. The heater coil may extend fully or partially around the circumference of the wick 28. In another embodiment, the heater coil is not in contact with the wick 28.

The heater 14 heats liquid in the wick 28 by thermal conduction. Alternatively, heat from the heater 14 may be conducted to the liquid by means of a heat conductive element or the heater 14 may transfer heat to the incoming ambient air that is drawn through the e-vaping device 60 during use, which in turn heats the liquid by convection.

In one embodiment, the wick comprises a ceramic material or ceramic fibers. As noted above, the wick 28 is at least partially surrounded by the heater 14. Moreover, in an embodiment, the wick 28 extends through opposed openings in the inner tube 62 such that end portions 29, 31 of the wick 28 are in contact with the liquid supply reservoir 22.

The wick 28 may comprise a plurality or bundle of filaments. In one embodiment, the filaments may be generally aligned in a direction transverse to the longitudinal direction of the e-vaping device, but the example embodiments are not limited to this orientation. In one embodiment, the structure of the wick 28 is formed of ceramic filaments capable of drawing liquid via capillary action via interstitial spacing between the filaments to the heater 14. The wick 28 can include filaments having a cross-section which is generally cross-shaped, clover-shaped, Y-shaped or in any other suitable shape.

The wick 28 includes any suitable material or combination of materials. Examples of suitable materials are glass filaments and ceramic or graphite based materials. Moreover, the wick 28 may have any suitable capillarity accommodate aerosol generating liquids having different liquid physical properties such as density, viscosity, surface tension and vapor pressure. The capillary properties of the wick 28, combined with the properties of the liquid, ensure that the wick 28 is always wet in the area of the heater 14 to avoid overheating of the heater 14.

Instead of using a wick, the heater can be a porous material of sufficient capillarity and which incorporates a resistance heater formed of a material having a high electrical resistance capable of generating heat quickly.

In one embodiment, the wick 28 and the fibrous medium 21 of the liquid supply reservoir 22 are constructed from an alumina ceramic. In another embodiment, the wick 28 includes glass fibers and the fibrous medium 21 includes a cellulosic material or polyethylene terephthalate.

In an embodiment, the power supply 1 includes a battery arranged in the e-vaping device 60 such that the anode is downstream of the cathode. A battery anode connector 4 contacts the downstream end of the battery. The heater 14 is connected to the battery by two spaced apart electrical leads 26 (shown in FIGS. 4, 6 and 8).

The connection between the uncoiled, end portions 27, 27' (see FIG. 5) of the heater 14 and the electrical leads 26 are highly conductive and temperature resistant while the heater 14 is highly resistive so that heat generation occurs primarily along the heater 14 and not at the contacts.

The battery may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, the e-vaping device 60 is usable until the energy in the power supply is depleted. Alternatively, the power supply 1 may be rechargeable and include circuitry allowing the battery to be chargeable by an external charging device. In that case, the circuitry, when charged, provides power for a desired (or alternatively a pre-determined) number of puffs, after which the circuitry must be re-connected to an external charging device.

The e-vaping device 60 also includes control circuitry including the puff sensor 16. The puff sensor 16 is operable to sense an air pressure drop and initiate application of voltage from the power supply 1 to the heater 14. The control circuitry can also include a heater activation light 48 operable to glow when the heater 14 is activated. In one embodiment, the heater activation light 48 comprises an LED 48 and is at an upstream end of the e-vaping device 60 so that the heater activation light 48 takes on the appearance of a burning coal during a puff. Moreover, the heater activation light 48 can be arranged to be visible to the adult vaper. In addition, the heater activation light 48 can be utilized for e-vaping system diagnostics. The light 48 can also be configured such that the adult vaper can activate and/or deactivate the light 48 for privacy, such that the light 48 would not activate during vaping if desired.

The at least one air inlet 44a is located adjacent the puff sensor 16, such that the puff sensor 16 senses air flow indicative of an adult vaper taking a puff and activates the power supply 1 and the heater activation light 48 to indicate that the heater 14 is working.

A control circuit is integrated with the puff sensor 16 and supplies power to the heater 14 responsive to the puff sensor 16, for example, with a maximum, time-period limiter.

Alternatively, the control circuitry may include a manually operable switch for an adult vaper to initiate a puff. The time-period of the electric current supply to the heater may be pre-set depending on the amount of liquid desired to be vaporized. The control circuitry may be programmable for this purpose. Alternatively, the circuitry may supply power to the heater as long as the puff sensor detects a pressure drop.

When activated, the heater 14 heats a portion of the wick 28 surrounded by the heater for less than about 10 seconds, more preferably less than about 7 seconds. Thus, the power cycle (or maximum puff length) can range in period from about 2 seconds to about 10 seconds (e.g., about 3 seconds to about 9 seconds, about 4 seconds to about 8 seconds or about 5 seconds to about 7 seconds).

In an embodiment, the liquid supply reservoir 22 includes a liquid storage medium 21 containing liquid material. In the embodiments shown in FIGS. 1, 4, 6, 8, 9 and 13, the liquid supply reservoir 22 is contained in an outer annulus 62 between inner tube 62 and outer tube 6 and between stopper 10 and the seal 15. Thus, the liquid supply reservoir 22 at least partially surrounds the central air passage 20 and the heater 14 and the wick 14 extend between portions of the liquid supply reservoir 22. The liquid storage material may be a fibrous material comprising cotton, polyethylene, polyester, rayon and combinations thereof. The fibers may have a diameter ranging in size from about 6 microns to about 15 microns (e.g., about 8 microns to about 12 microns or about 9 microns to about 11 microns). The liquid storage medium 21 may be a sintered, porous or foamed material. Also, the fibers may be sized to be irrespirable and can have a cross-section which has a y shape, cross shape, clover shape or any other suitable shape. In the alternative, the reservoir 22 may comprise a filled tank lacking a fibrous storage medium 21, such as further described with reference to FIGS. 15-17.

Also, the liquid material has a boiling point suitable for use in the e-vaping device 60. If the boiling point is too high, the heater 14 will not be able to vaporize liquid in the wick 28. However, if the boiling point is too low, the liquid may vaporize without the heater 14 being activated.

The liquid material may include a tobacco-containing material including volatile tobacco flavor compounds which are released from the liquid upon heating. The liquid may also be a tobacco flavor containing material or a nicotine-containing material. Alternatively, or in addition, the liquid may include a non-tobacco material. For example, the liquid may include water, solvents, active ingredients, ethanol, plant extracts and natural or artificial flavors. The liquid may further include an aerosol former. Examples of suitable aerosol formers are glycerine, propylene glycol, etc.

Figure 4:
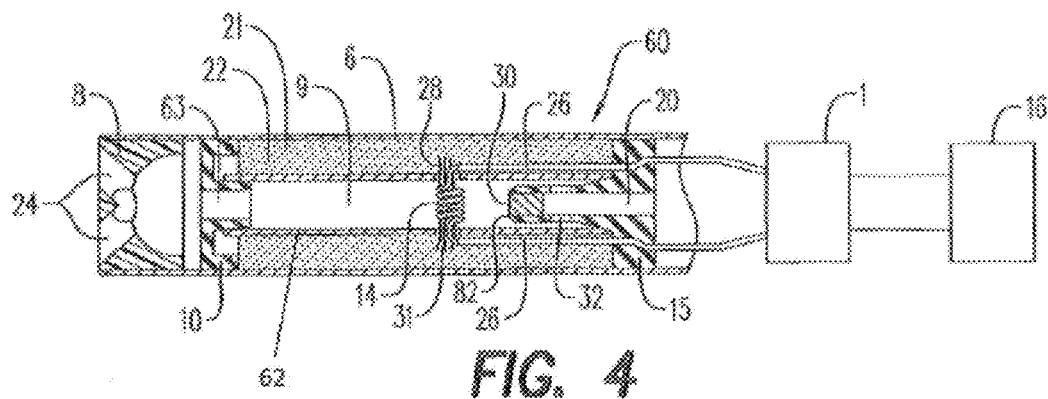
FIG. 4 is a cross-sectional view of an embodiment wherein an e-vaping device includes an air flow diverter, in accordance with an example embodiment.

In use, liquid material is transferred from the liquid supply reservoir 22 and/or liquid storage medium 21 in proximity of the 14 heater by capillary action in the wick 28. In one embodiment, the wick 28 has a first end portion 29 and a second opposite end portion 31 as shown in FIG. 4. The first end portion 29 and the second end portion 31 extend into opposite sides of the liquid storage medium 21 for contact with liquid material contained therein. The heater 14 at least partially surrounds a central portion of the wick 28 such that when the heater 14 is activated, the liquid in the central portion of the wick 28 is vaporized by the heater 14 to vaporize the liquid material and form an aerosol.

One advantage of an embodiment is that the liquid material in the liquid supply reservoir 22 is protected from oxygen (because oxygen cannot generally enter the liquid storage portion via the wick) so that the risk of degradation of the liquid material is significantly reduced. Moreover, in some embodiments in which the outer tube 6 is not clear, the liquid supply reservoir 22 is protected from light so that the risk of degradation of the liquid material is significantly reduced. Thus, a high level of shelf-life and cleanliness can be maintained.

As shown in FIGS. 2A and 2B, the mouth end insert 8, includes at least two diverging outlets 24 (e.g., 3, 4, 5 or more). The outlets 24 of the mouth end insert 8 are located at ends of off-axis passages 80 and are angled outwardly in relation to the longitudinal direction of the e-vaping device 60 (i.e., divergently). As used herein, the term "off-axis" denotes at an angle to the longitudinal direction of the e-vaping device. Also, the mouth end insert (or flow guide) 8 may include outlets uniformly distributed around the mouth end insert 8 so as to substantially uniformly distribute aerosol in an adult vaper's mouth during use. Thus, as the aerosol passes into an adult vaper's mouth, the aerosol enters the mouth and moves in different directions so as to provide a full mouth feel as compared to e-vaping devices having an on-axis single orifice which directs the aerosol to a single location in an adult vaper's mouth.

In addition, the outlets 24 and off-axis passages 80 are arranged such that droplets of unaerosolized liquid material carried in the aerosol impact interior surfaces 81 at mouth end insert and/or interior surfaces of the off-axis passages such that the droplets are removed or broken apart. In an embodiment, the outlets of the mouth end insert are located at the ends of the off-axis passages and are angled at 5 to 60 degrees with respect to the central axis of the outer tube 6 so as to more completely distribute aerosol throughout a mouth of an adult vaper during use and to remove droplets.

Preferably, each outlet has a diameter of about 0.015 inch to about 0.090 inch (e.g., about 0.020 inch to about 0.040 inch or about 0.028 inch to about 0.038 inch). The size of the outlets 24 and off-axis passages 80 along with the number of outlets can be selected to adjust the resistance to draw (RTD) of the e-vaping device 60, if desired.

As shown in FIG. 1, an interior surface 81 of the mouth end insert 8 can comprise a generally domed surface. Alternatively, as shown in FIG. 2B, the interior surface 81' of the mouth end insert 8 can be generally cylindrical or frustoconical, with a planar end surface. The interior surface is substantially uniform over the surface thereof or symmetrical about the longitudinal axis of the mouth end insert 8. However, in other embodiments, the interior surface can be irregular and/or have other shapes.

The mouth end insert 8 is integrally affixed within the tube 6 of the cartridge 70. Moreover, the mouth end insert 8 may be formed of a polymer selected from the group consisting of low density polyethylene, high density polyethylene, polypropylene, polyvinylchloride, polyetheretherketone (PEEK) and combinations thereof. The mouth end insert 8 may also be colored if desired.

In an embodiment, the e-vaping device 60 also includes various embodiments of an air flow diverter or air flow diverter means, which are shown in FIGS. 4, 6, 8, 13, 15-17. The air flow diverter is operable to manage air flow at or about around the heater so as to abate a tendency of drawn air to cool the heater, which could otherwise lead to diminished aerosol output.

Figure 5:
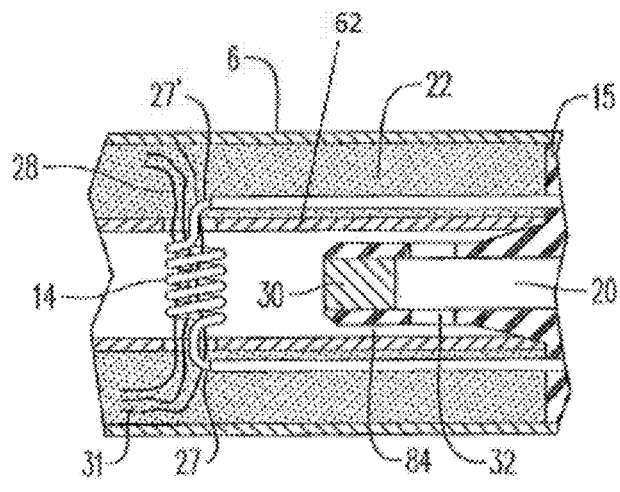
FIG. 5 is an enlarged view of the air flow diverter of the e-vaping device of FIG. 4, in accordance with an example embodiment.
Figure 6:
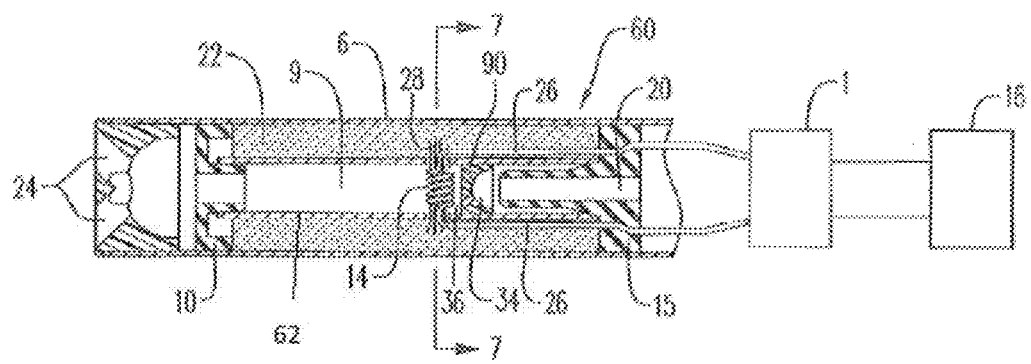
FIG. 6 is a cross-sectional view of an embodiment wherein an e-vaping device includes an air flow diverter, in accordance with an example embodiment.

In one embodiment, as shown in FIGS. 4 and 5, the e-vaping device 60 can include an air flow diverter comprising an impervious plug 30 at a downstream end 82 of the central air passage 20 in seal 15. The central air passage 20 is an axially extending central passage in seal 15 and inner tube 62. The seal 15 seals the upstream end of the annulus between the outer and inner tubes 6, 62. The air flow diverter may include at least one radial air channel 32 directing air from the central passage 20 outward toward the inner tube 62 and into an outer air passage 9 defined between an outer periphery of a downstream end portion of the seal 15 and the inner wall of inner tube 62.

The diameter of the bore of the central air passage 20 is substantially the same as the diameter of the at least one radial air channel 32. Also, the diameter of the bore of the central air passage 20 and the at least one radial air channel 32 may range from about 1.5 mm to about 3.5 mm (e.g., about 2.0 mm to about 3.0 mm). Optionally, the diameter of the bore of the central air passage 20 and the at least one radial air channel 32 can be adjusted to control the resistance to draw of the e-vaping device 60. In use, the air flows into the bore of the central air passage 20, through the at least one radial air channel 32 and into the outer air passage 9 such that a lesser portion of the air flow is directed at a central portion of the heater 14 so as to reduce or minimize the aforementioned cooling effect of the airflow on the heater 14 during heating cycles. Thus, incoming air is directed away from the center of the heater 14 and the air velocity past the heater is reduced as compared to when the air flows through a central opening in the seal 15 oriented directly in line with a middle portion of the heater 14.

In another embodiment, as shown in FIGS. 6 and 7, the air flow diverter can be in the form of a disc 34 positioned between the downstream end of seal 15 and the heater 14. The disc 34 includes at least one orifice 36 in a transverse wall at a downstream end of an outer tubular wall 90. The at least one orifice 36 may be off-axis so as to direct incoming air outward towards the inner wall of tube 62. During a puff, the disc 34 is operable to divert air flow away from a central portion of the heater 14 so as to counteract the tendency of the airflow to cool the heater as a result of a strong or prolonged draw by an adult vaper. Thus, the heater 14 is substantially reduced or prevented from cooling during heating cycles so as to reduce or prevent a drop in the amount of aerosol produced during a puff.

As shown in FIGS. 13 and 14, the heater 14 is oriented longitudinally within the inner tube 62 and the disc 34 includes at least one orifice 36 arranged to direct air flow non-centrally and/or radially away from the centralized location of the heater 14. In embodiment where the heater 14 is oriented longitudinally within the inner tube 62 and adjacent an inner wall of the inner tube 62, the orifices 36 can be arranged to direct at least a portion of the airflow away from the heater 14 so as to abate the cooling effect of the air flow upon the heater 14 during a power cycle and/or be arranged to decelerate the air flow to achieve the same effect.

In yet another embodiment, as shown in FIG. 8, the air flow diverter comprises a frustoconical section 40 extending from the downstream end 82 of a shortened central air passage 20. By shortening the central passage 20 as compared to other embodiments, the heater 14 is positioned farther away from the central passage 20 allowing the air flow to decelerate before contacting the heater 14 and lessen the tendency of the air flow to cool the heater 14. Alternatively, the heater 14 can be moved closer to the mouth end insert 8 and farther away from the central air passage 20 to allow the air flow time and/or space sufficient to decelerate to achieve the same cooling-abatement effect.

The addition of the frustoconical section 40 provides a larger diameter bore size which can decelerate the air flow so that the air velocity at or about the heater 14 is reduced so as to abate the cooling effect of the air on the heater 14 during puff cycles. The diameter of the large (exit) end of the frustoconical section 40 ranges from about 2.0 mm to about 4.0 mm, and preferably about 2.5 mm to about 3.5 mm.

The diameter of the bore of the central air passage 20 and the diameter of the smaller and/or larger end of the frustoconical section 40 can be adjusted to control the resistance to draw of the e-vaping device 60.

The air flow diverter of the various embodiments channels the air flow by controlling the air flow velocity (its speed and/or the direction of the air flow). For example, the air flow diverter can direct air flow in a particular direction and/or control the speed of the air flow. The air flow speed may be controlled by varying the cross sectional area of the air flow route. Air flow through a constricted section increases in speed while air flow through a wider section decreases speed.

In an embodiment, the e-vaping device 60 may be about the same size as a conventional cigarette. In some embodiments, the e-vaping device 60 can be about 80 mm to about 110 mm long, preferably about 80 mm to about 100 mm long and about 7 mm to about 8 mm in diameter. For example, in an embodiment, the e-vaping device is about 84 mm long and has a diameter of about 7.8 mm.

In one embodiment, the e-vaping device 60 of FIGS. 1, 4, 6 and 8 can also include a filter segment upstream of the heater 14 and operable to restrict flow of air through the e-vaping device 60. The addition of a filter segment can aid in adjusting the resistance to draw.

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. In one embodiment, the material is light and non-brittle.

As shown in FIG. 9, the e-vaping device 60 can also include a sleeve assembly 87 removably and/or rotatably positioned about the outer tube 6 adjacent the first section 70 of the e-vaping device 70. Moreover, the sleeve assembly 87 insulates at least a portion of the first section 70 so as to maintain the temperature of the aerosol prior to delivery to the adult vaper. In an embodiment, the sleeve assembly 87 is rotatable about the e-vaping device 60 and includes spaced apart slots 88 arranged transversely about the sleeve assembly such that the slots 88 line up with the air inlets 44 in the first section 70 to allow air to pass into the e-vaping device 60 when an adult vaper draws a puff. Before or during vaping, the adult vaper can rotate the sleeve assembly 87 such that the air inlets 44 are at least partially blocked by the sleeve assembly 87 so as to adjust the resistance to draw and/or ventilation of the e-vaping device 60.

The sleeve assembly 87 is made of silicone or other pliable material so as to provide a soft mouthfeel to the adult vaper. However, the sleeve assembly 87 may be formed in one or more pieces and can be formed of a variety of materials including plastics, metals and combinations thereof. In an embodiment, the sleeve assembly 87 is a single piece formed of silicone. The sleeve assembly 87 may be removed and reused with other e-vaping devices or can be discarded along with the first section 70. The sleeve assembly 87 may be any suitable color and/or can include graphics or other indicia.

As shown in FIG. 10, the e-vaping device 60 can also include an aroma strip 89 located on an outer surface 91 of at least one of the first section 70 and the second section 72. Alternatively, the aroma strip 89 can be located on a portion of the sleeve assembly 87. The aroma strip 89 is located between the battery of the device and the heater such that the aroma strip 89 is adjacent an adult vaper's nose during vaping. The aroma strip 89 may include a flavor aroma gel, film or solution including a fragrance material that is released before and/or during vaping. In one embodiment, the flavor aroma of the gel, fluid and/or solution can be released by the action of a puff which may open a vent over the aroma strip when positioned inside the first section 70 (not shown). Alternatively, heat generated by the heater 14 can cause the release of the aroma.

In one embodiment, the aroma strip 89 can include tobacco flavor extracts. Such an extract can be obtained by grinding tobacco material to small pieces and extracting with an organic solvent for a few hours by shaking the mixture. The extract can then be filtered, dried (for example with sodium sulfate) and concentrated at controlled temperature and pressure. Alternatively, the extracts can be obtained using techniques known in the field of flavor chemistry, such as the Solvent Assisted Flavor Extraction (SAFE) distillation technique (Engel et al. 1999), which allows separation of the volatile fraction from the non-volatile fraction. Additionally, pH fractionation and chromatographic methods can be used for further separation and/or isolation of specific compounds. The intensity of the extract can be adjusted by diluting with an organic solvent or water.

The aroma strip 89 can be a polymeric or paper strip to which the extract can be applied, for example, using a paintbrush or by impregnation. Alternatively, the extract can be encapsulated in a paper ring and/or strip and released manually by the adult vaper, for example by squeezing during vaping the aroma strip 89.

As shown in FIGS. 11 and 12, in an alternative embodiment, the e-vaping device of FIGS. 1, 4, 6 and 8 can includes a mouth end insert 8 having a stationary piece 27 and a rotatable piece 25. Outlets 24, 24' are located in each of the stationary piece 27 and the rotatable piece 25. One or more of the outlets 24, 24' align as shown to allow aerosol to enter an adult vaper's mouth. However, the rotatable piece 25 can be rotated within the mouth end insert 8 so as to at least partially block one or more of the outlets 24 in the stationary mouth end insert 27. Thus, the consumer can adjust the amount of aerosol drawn with each puff. The outlets 24, 24' can be formed in the mouth end insert 8 such that the outlets 24, 24' diverge to provide a fuller mouth feel during inhalation of the aerosol.

In another embodiment, the air flow diverter comprises the addition of a second wick element adjacent to but just upstream of the heater 14. The second wick element diverts portions of the air flow about the heater 14.

Figure 15:
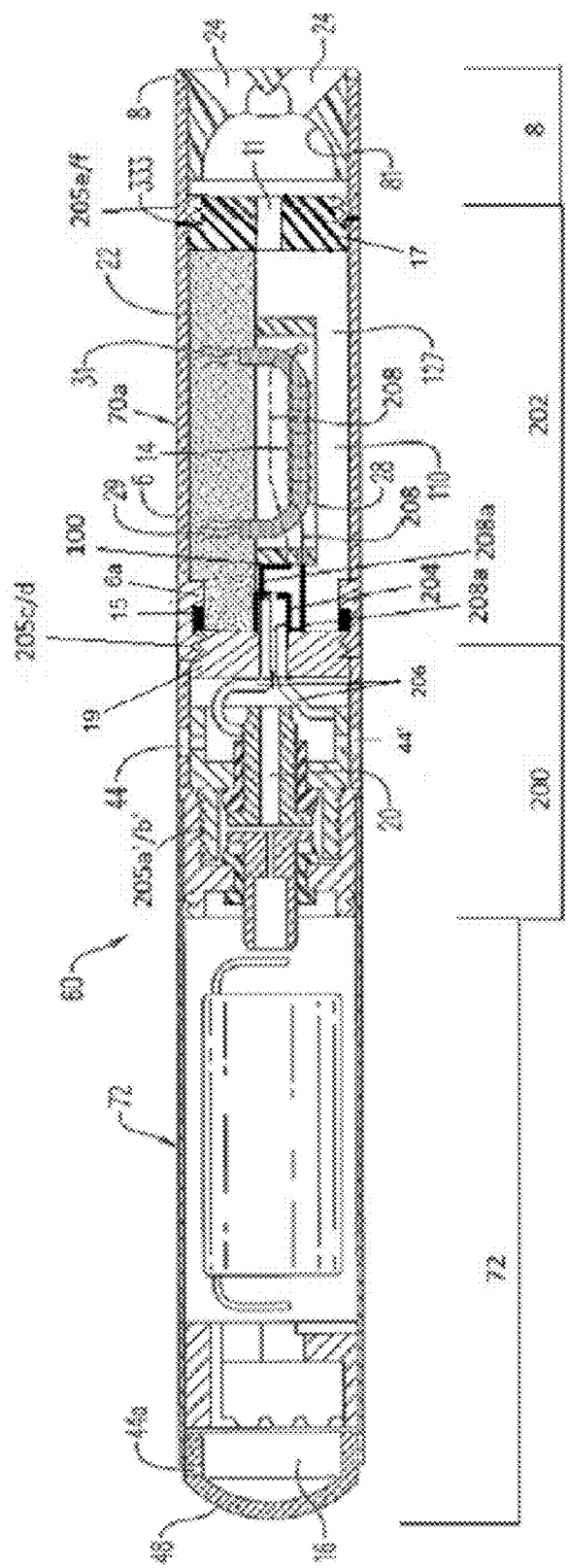
FIG. 15 is a cross-sectional view of an embodiment wherein an e-vaping device includes an air flow diverter, in accordance with an example embodiment.

In another embodiment, as shown in FIG. 15, the e-vaping device 60 comprises a tank (or first section) 70*a*, sometimes referred to as an "e-vaping tank," and a reusable fixture (or second section) 72, which may be coupled together at threaded connection 205*a*'/b' (205*a*' being the male threaded connection and 205*b*' being the female threaded connection) via the use of an adapter 200 (described below in detail). Threaded connections 205*a*'/b' may have non-standard threads, as described in FIGS. 3B-3D. The second section 72 can be constructed in accordance with the teachings above regarding the other embodiments such as that shown and described with respect to FIG. 1.

Still referring to FIG. 15, in this embodiment, the first section 70*a* may be reusable. Alternatively, first section 70*a* may be disposable. First section 70*a* may include an outer tube 6 (or casing) extending in a longitudinal direction. The first section 70*a* may have two major portions, which may include tank 202, and mouth piece 8, where these two sections may be connected via threaded connections 205*e/f* (i.e., respective male and female threaded connections). Threaded connections 205*e/f* may have non-standard threads, as shown in FIGS. 3B-3D. First section 70*a* may include liquid supply reservoir in the form of a truncated cylindrical tank reservoir 22. Tank reservoir 22 may include a separately formed, self-supporting (discrete) hollow body constructed of a heat-resistant plastic or woven fiberglass. In an embodiment, the tank reservoir 22 can be generally in the form of elongate partial cylinder, one side of which is truncated. In an embodiment, the tank reservoir 22 has a transverse dimension, such as in the direction of arrow "x" in FIG. 16, and is truncated such that the aforementioned transverse dimension is approximately two-thirds of the diameter of the tank reservoir 22. The aforementioned transverse dimension may vary in other embodiments, depending on design requirements such as a desired capacity of the tank or a need for space within the casing 6 for heaters and for channeling airflow. For example, in the embodiment shown in FIG. 15, the tank reservoir 22 has a semi-circular cross-section or a transverse dimension equal to one-half the tank diameter. In an alternative embodiment, tank reservoir 22 may be an annulus located around the inner periphery of tube 6.

The adapter 200 (sometimes referred to as a "bridge," or a "connector") may be located between the reusable fixture 72 and the tank 70*a*. The adapter 200 may be used to connect a female threaded connection on reusable section 72 to a female threaded connection on tank 202, as shown in FIG. 15. The adapter 200 may include the central air passage 20 and air inlets 44/44'. Electrical leads 206 may extend from adapter 200 into male stub 204 in order to make electrical contact with electrical connections 208*a* that are connected to electrical leads 208 which provide power to heater 14. Adapter 200 may be connected to reusable section 72 via the threaded connections 205*a*'/b'. Adapter 200 may be connected to tank 70*a* via threaded connections 205*c/d* (i.e., respective male and female threaded connections). Threaded connections 205*a*'/b' and 205*c/d* may have non-standard threads, as shown in FIGS. 3B-3D.

In one embodiment, the tank reservoir 22 can be constructed separate from the casing 6 and comprise a longitudinally extending planar panel 101 and an arcuate, longitudinally extending panel 103. The arcuate panel 103 may conform or mate with an interior surface 127 of the outer tube 6. It is envisioned that the tank reservoir 22 may be held in place against the interior 127 of the outer casing 6 by conveniences such as spaced ridges 333 and 333' at predetermined desired (or, a alternatively predetermined) locations along the interior 127 of the outer casing 6, a friction fit or a snap fit or other convenience. End wall 17 may seal one end of tank reservoir 22. Seal 15 may fit between stub 6*a* and the end wall 19 of adapter 200 to assist in sealing the other end of the tank reservoir 22. Seal 15 may be made of an absorbent material to absorb any liquid that might escape inadvertently from the tank reservoir 22. Mouthpiece 8 may screw onto an end of tank 202 via threaded connections 205*e/f* (i.e., respective male and female threaded connections). End wall 19 may screw onto the other end of tank 202 via threaded connections 205*c/d* (i.e., respective male and female threaded connections). Threaded connection 205*c/d* and 205*e/f* may have threads with a non-standard pitch, as shown in FIGS. 3B-3D. End wall 17 would be each provided apertures 11 to allow air and/or aerosol to pass therethrough.

In one embodiment, a wick 28 may be in communication with the interior of the supply reservoir 22 and in communication with a heater 14 such that the wick 28 draws liquid via capillary action from the tank reservoir 22 into proximity of the heater 14. As described previously, the wick 28 is a bundle of flexible filaments whose end portions 29 and 31 are disposed within the confines of the tank reservoir 22. The contents of the liquid supply reservoir 22 may be a liquid, as previously described, together with the end portions 29, 31 of the wick 28. The end portions 29, 31 of the wick 28 occupy substantial portions of the tank interior such that orientation of the vaping article 60 does not impact the ability of the wick 28 to draw liquid. Optionally, the tank reservoir 22 may include filaments or gauze or a fibrous web to maintain distribution of liquid within the tank reservoir 22.

As described previously, the heater 14 may comprise a coil winding of electrically resistive wire about a portion of the wick 28. Instead or in addition, the heater may comprise a single wire, a cage of wires, printed "wire," metallic mesh, or other arrangement instead of a coil. The heater 14 and the associated wick portion 28 may be disposed centrally of the planar panel 101 of the tank reservoir 22 as shown in FIG. 16, or could be placed at one end portion thereof or may be one or two or more heaters 14 disposed either centrally or at opposite end portions of the planar panel 101.

Figure 16:
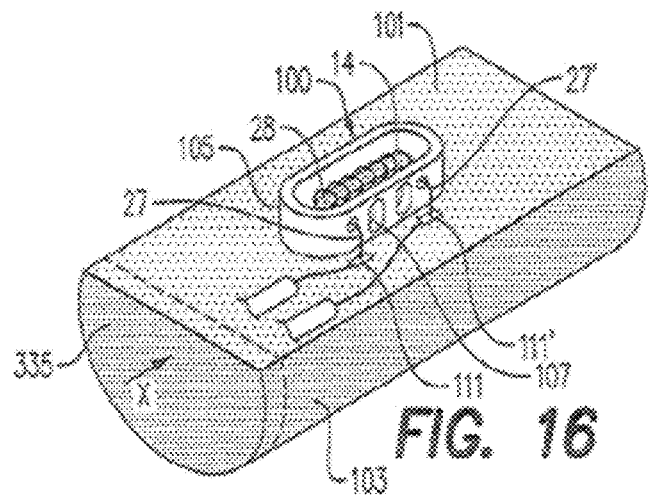
FIG. 16 is an enlarged view of an air flow diverter and tank reservoir of the e-vaping device of FIG. 15, in accordance with an example embodiment.

Referring now to FIGS. 15 and 16, in an embodiment, a flow diverter 100 is provided adjacent the heater 14. The diverter 100 may take the form of a generally oval shield or wall 105 extending outwardly from the plane of the planar panel 101 and proximate to the heater 14 and the wick 28 such that an approaching air stream is diverted away from the heater 14 so that the amount of air drawn directly across the heater is reduced in comparison the arrangements lacking a flow diverter 100.

The oval wall 105 is open ended so that when the heater 14 is activated to freshly produce aerosol in its proximity, such supersaturated aerosol may be withdrawn from the confines of the diverter 100. Not wishing to be bound by theory, such arrangement releases aerosol by utilizing the drawing action or venturi effect of the air passing by the heater 14 and the open ended diverter 100. Optionally, holes 107 are provided in the wall 105 of the diverter 100 so that the drawing action of the air tending to withdraw aerosol from the confines of the diverter 100 does not work against a vacuum. These holes 107 may be sized to provide an optimal amount of air to be drawn into the confines of the diverter 100. Thereby, the amount of air being drawn into contact with the heater 14 is reduced and controlled, and a substantial portion of the approaching air stream is diverted and by-passes the heater 14, even during aggravated draws upon the e-vaping device 60.

In addition, the holes 107 may be utilized for routing of end portions 27, 27' of the heater 14 or separate holes or notches may be provided. In the embodiment of FIG. 16, the end portions 27, 27' of the heater 14 and the electric leads 26 and 26' are connected at electric contacts 111, 111' established on the planar panel 101 adjacent the location of the diverter 100. The electrical contacts 111, 111' may instead be established on the wall 105' itself, as shown in FIG. 17.

Referring back to FIG. 16, the oval diverter shield 105 is symmetrical along the longitudinal axis such that the diverter 100 may be placed in the orientation as shown in FIG. 16 or 180 degrees from that orientation, which facilitates manufacture and assembly of the vaping article 60.

Figure 17:
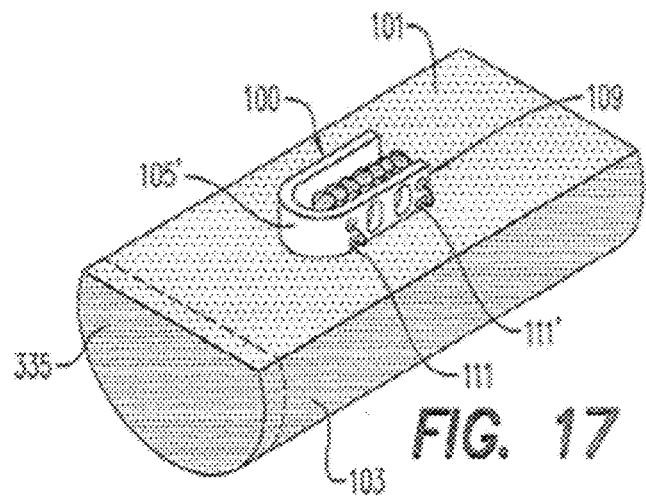
FIG. 17 is an enlarged view of an alternate air flow diverter and tank reservoir of the e-vaping device of FIG. 15, in accordance with an example embodiment.

Referring now to the FIG. 17, the diverter 100 may be configured instead to have an oval wall 105' that includes an open-ended downstream portion 109, which further facilitates the release of aerosol from about the heater 14. It is envisioned that the wall 105 of the diverter 100 may take a form of a shallow "u" or "v" and may include an arched portion at least partially superposing the heater 14. In the embodiments shown in FIGS. 15, 16 and 17, the oval shield wall 105 is oriented with its longitudinal axis generally parallel to the longitudinal axis of the vaping article 60.

Figure 18:
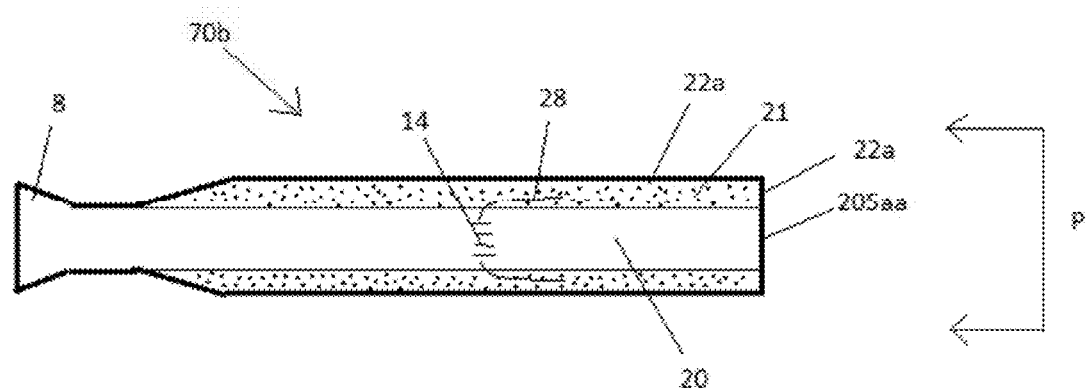
FIG. 18 is a simplified diagram of an e-vaping tank, in accordance with an example embodiment.

As shown in FIG. 18, a simplified diagram of another e-vaping tank 70*b* is depicted. The tank 70*b* may have identical internal components as those shown in tank 70*a* (FIG. 15), and therefore only the differences between tank 70*b* and tank 70*a* are described. The tank 70*b* may include an annulus liquid reservoir. The general shape of the mouthpiece 8 may also be different. The tank 70*b* may have a male threaded connection 205*aa* that is capable of connecting directly to the female threaded connection 205*b'* of reusable section 72, such that an adapter is not required. Male threaded connection 205*aa* may have non-standard threads, as described in FIGS. 3B-3D. The tank 70*b* may be refillable via a liquid reservoir opening 22*a* using any commercially-available liquid fluid 21 in order to continually reuse tank 70*b*.

Figure 19:
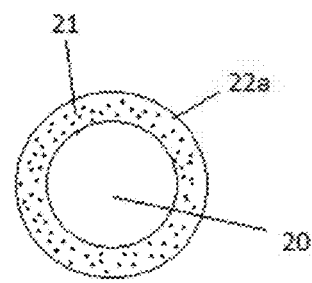
FIG. 19 is a side-view of the e-vaping tank of FIG. 18.

FIG. 19 shows a side view of the e-vaping tank 70*b* of FIG. 18 (from perspective "P," shown in FIG. 18). In particular, FIG. 19 shows the liquid reservoir opening 22*a*, which may be an annulus positioned around central air passage 20, that provides an opening for an adult vaper to access the inside of tank 70*b* and pour the liquid material 21 into the liquid supply reservoir 22.

Figure 20:
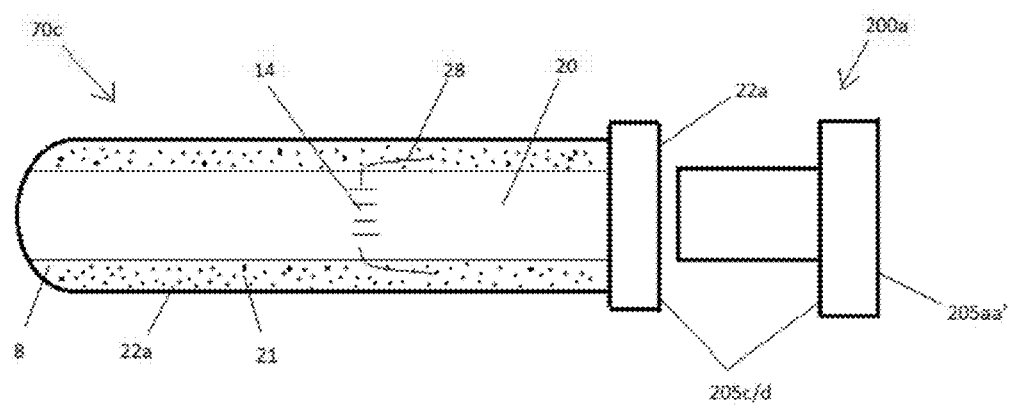
FIG. 20 is another simplified view of an e-vaping tank, in accordance with an example embodiment.

FIG. 20 shows an example of another e-vaping tank 70*c*. The tank 70*b* may have identical internal components as those shown in tank 70*a* (FIG. 15), and therefore only the differences between tank 70*b* and tank 70*a* are described. The tank 70*c* may have a cap 200*a* that seals an open end (at reservoir opening 22*a*) of tank 70*c*. Cap 200*a* may have threaded connections 205*c/d* (i.e., respective male and female threaded connections) holding cap 200*a* onto tank 70*c*. Cap 200*a* may also have a male threaded connection 205*aa'* that is connectable to female threaded connection 205*b'* of reusable section 72 (FIG. 15). Threaded connections 205*c/d* and 205*aa'* may have non-standard threads, as described in FIGS. 3B-3D. The cap 200*a* may screw onto the end of tank 70*c*, following a re-filling of tank 70*c* with liquid material 21, to allow tank 70*c* to be easily transported without spilling of the liquid material 21 from liquid supply reservoir 22. Reservoir 22 may also be an annulus-type reservoir.

Figure 21:
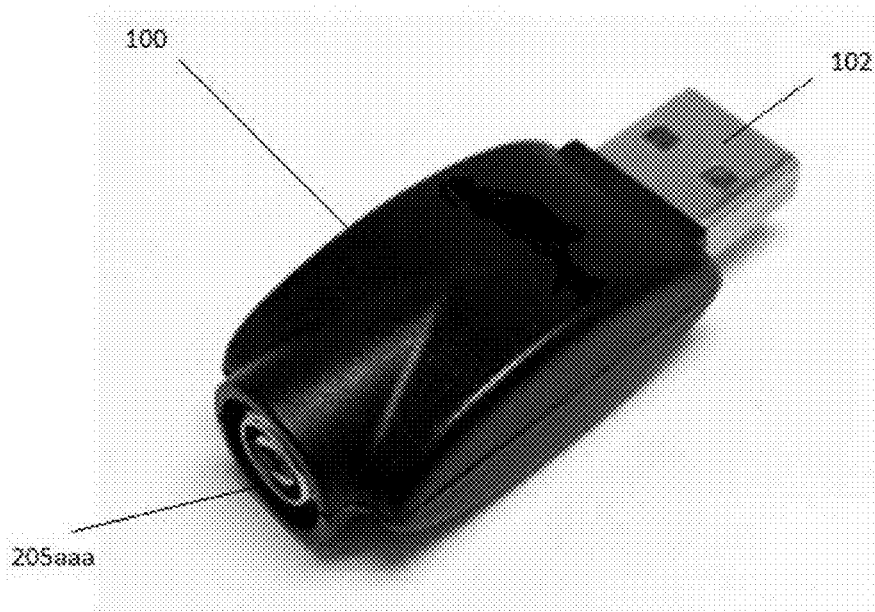
FIG. 21 is a charger for an e-vaping device, in accordance with an example embodiment.

FIG. 21 shows a charger 100 for an e-vaping device, such as any of the e-vaping devices described herein. The charger 100 may include an electrical connection (such as a USB connection 102) that connects to a power source, such as a DC power source. It should be understood that the charger 100 may alternatively connect to an AC power source. The charger 100 may include a threaded connection 205*aaa* that may be used to electrically connect charger 100 to reusable section 72 in order to charge the battery 1 for extended use.

Threaded connection 205*aaa* may have non-standard threads, as described in FIGS. 3B-3D.

Figure 22:
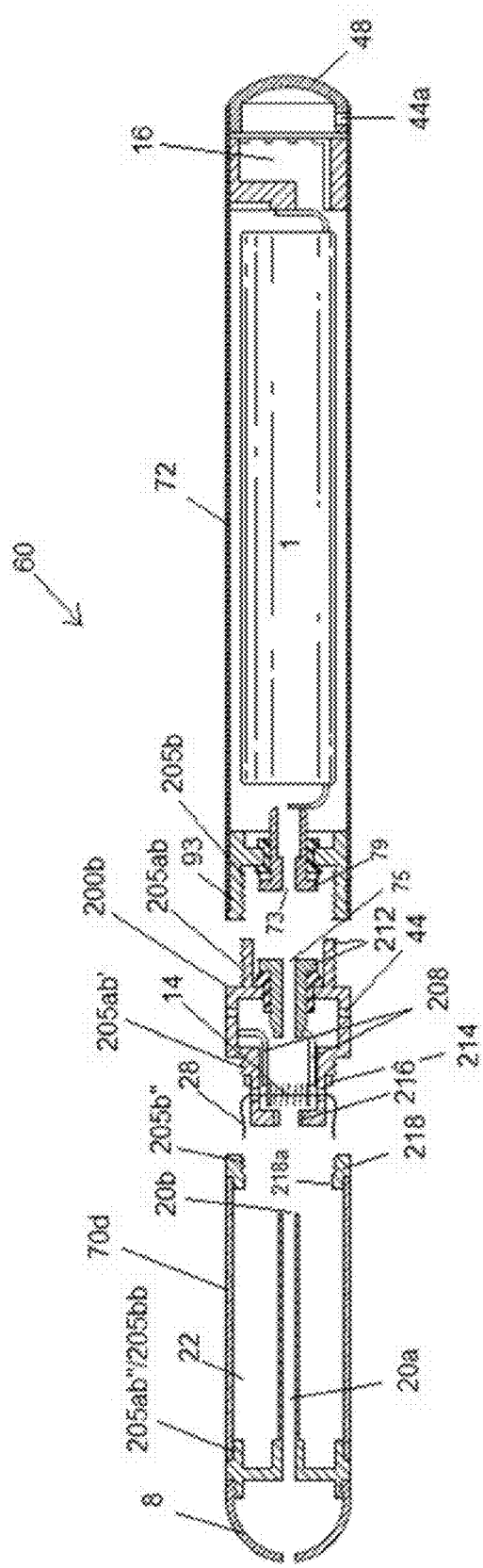
FIG. 22 is an exploded view of an e-vaping device with an adapter, in accordance with an example embodiment.

FIG. 22 shows a cross-section of another embodiment of an e-vaping device 60 including an e-vaping tank 70*d* with an annulus reservoir 22. Contrary to tanks 70*a* (FIG. 15), 70*b* (FIG. 18) and 70*c* (FIG. FIG. 20), e-vaping tank 70*d* may merely be a tank, devoid of a wick or heater. Also, at least a portion of reservoir 22 may have a transparent wall so that an adult vaper may monitor an amount of liquid material in the reservoir 22. In this embodiment, adapter 200*b* may contain a heater 14, and one or more wicks 28 may protrude laterally near an end of the adapter 200*b* to become exposed and submersed in a liquid material that may fill reservoir 22 of tank 70*d*. Electrical leads 208 may electrically connect heater 14 to inner terminal 212*a* and outer terminal 212*b*. An outer surface of outer terminal 212*b* may form a male threaded connection 205*ab* that may mate with a female threaded connection 205*b* within reusable section 72. Threaded connections 205*ab/b* may have non-standard threads, as described in FIGS. 3B-3D. Terminals 212*a/b* of adapter 200*b* may be in electrical contact with terminals 79/93 (of section 72), respectively, in order to allow battery 1 to energize heater 14 when puff sensor 16 detects an adult vaper inhaling from mouthpiece 8 (see a more detailed discussion of the performance of these electrical contacts during operation of the e-vaping device 60, below). As will be understood, the terminal 93 is electrically connected to distal end of battery 1.

Figure 23:
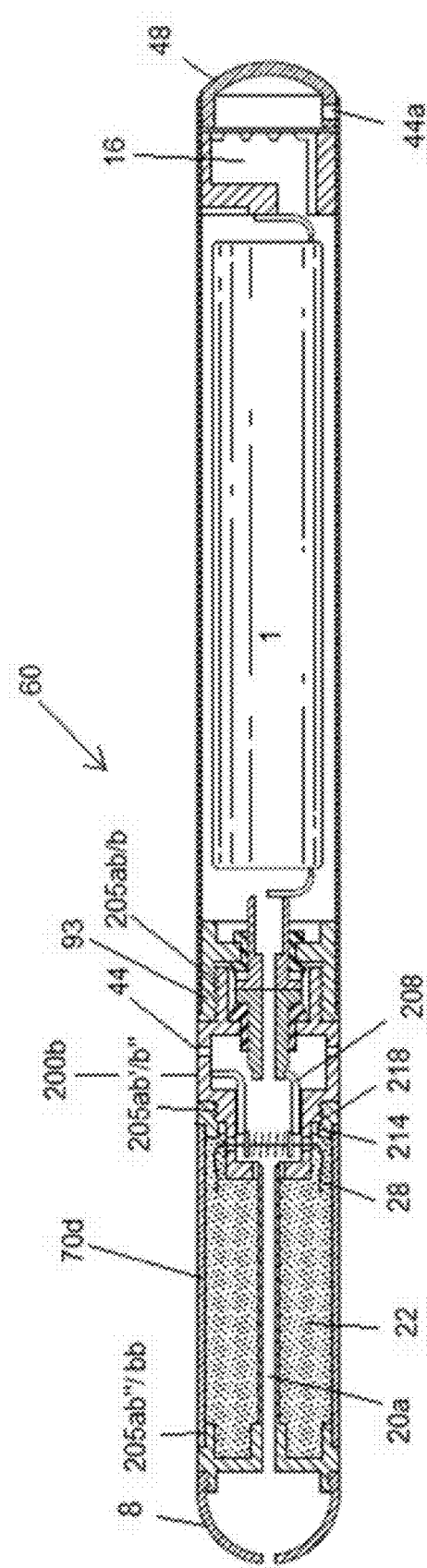
FIG. 23 is a side-view of the assembled e-vaping device of FIG. 22, in accordance with an example embodiment.

An air passage 20 may run longitudinally through tank 70*d* and adapter 200*b*. Air inlets 44/44' may penetrate the walls of adapter 200*b* and be fluidly connected to air passage 20. The adapter 200*b* may include another male threaded connection 205*ab*' that may mate with female threaded connections 205*b*" on tank 70*d* (see the assembled e-vaping device 60 in FIG. 23). Threaded connections 205*ab*'/b" may have non-standard threads, as shown in FIGS. 3B-3D. Seals 214/216 may be provided within adapter 200*b* to contain liquid material within the adapter 200*b*. Specifically, when adapter 200*b* in inserted into tank 70*d*, seal 214 may press against inner wall 218*a* of stubs 218 on the interior of the tank 70*d*. Meanwhile, a distal open end 20*b* of tube 20*a* (running longitudinally through a portion of tank 70*d*) may fit between seal 216. The combination of seal 214 and seal 216 prevents spillage of the liquid material outside of the e-vaping device 60.

Mouthpiece 8 may screw onto an end of tank 70*d* via threaded connections 205*ab*"/bb (205*ab*" being a male threaded connection, and 205*bb* being a female threaded connection). Threaded connections 205*ab*"/bb may have non-standard threads, as shown in FIGS. 3B-3D.

In operation, with e-vaping device 60 in an assembled configuration (see FIG. 23), an adult vaper may place their mouth on mouthpiece 8 and inhale. This inhalation may cause an internal pressure drop inside e-vaping device 60 that may cause an inlet air flow to enter device 60 via air inlets 44/44'. The internal pressure drop may also cause an internal pressure drop within reusable section 72 as air is drawn through air inlet 44*a* (via an air flow path traveling through through-holes 73/75 fluidly connecting adapter 200*b* and section 72). The internal pressure drop formed in section 72 may be sensed by puff sensor 16. The puff sensor 16 may then operate to close an electrical circuit that includes terminal 79, battery 1 and terminal 93, where terminals 79/93 (of section 72) are in electrical contact with terminals 212*a/b* (of adapter 200*b*), respectively. In turn, electrical leads 208 carry an electrical current to heater 14 in order to energize the heater 14. The energized heater 14 in turn heats and vaporizes liquid material that is drawn toward the heater 14 via wicks 28.

As the adult vaper continues to inhale and draw an air flow through air passage 20, the vaporized liquid material becomes entrained in the air flow which then passes through tube 20*a* of tank 70, through mouthpiece 8, and into the adult vaper's mouth.

Based on the embodiments described above, it should be understood that the non-standard male and female threaded connections (described in any of FIGS. 1, 3B-3D, 15, and 18-22) may be reversed between e-vaping elements. That is to say, a non-standard male threaded connection may be a non-standard female threaded connection, and a non-standard female threaded connection may be a non-standard male threaded connection. Furthermore, a male or female non-standard threaded connection may be outfitted on any at least one end (or, both ends) of any other e-vaping element that is described above to accompany an e-vaping device. Lastly, while the threaded connections disclosed in FIGS. 1, 3B-3D, 15, and 18-22 may each be non-standard threaded connections, it should be understood that each mateable threaded connection pair may be uniquely non-standard. That is to say, each mateable threaded connection pair may have a unique pitch that may be different from some, or all, of the other mateable threaded connection pairs.

Figure 24:
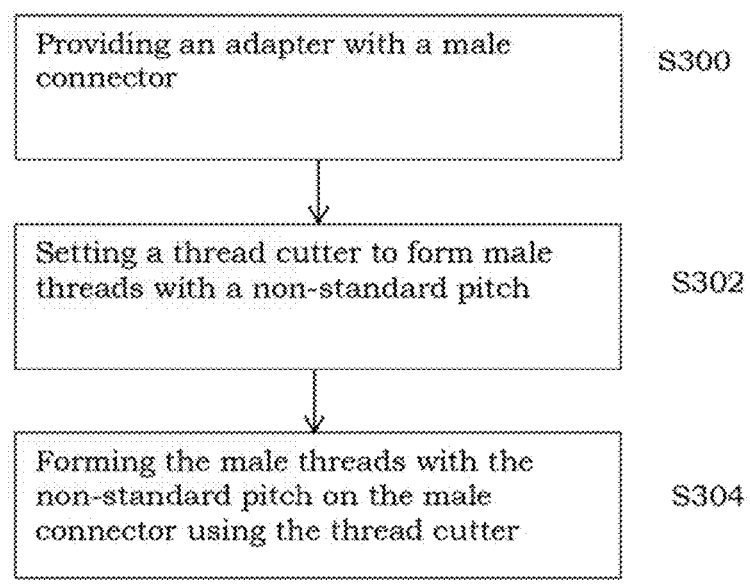
FIG. 24 shows a method of making an adapter 200, in accordance with an example embodiment.

FIG. 24 shows a method of making an adapter 200, in accordance with an example embodiment. The method may include a step S300 of providing an adapter 200 with a male threaded connection 205*a*' (see at least adapter 200 of FIG. 15). In step 302, a thread cutter may be set in order to form male threads with a non-standard pitch (in accordance with FIGS. 3B-3D) on the male threaded connection 205*a*'. In step S304, the thread cutter may be used to form the male threads with the non-standard pitch on the male threaded connection 205*a*'.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. An e-vapor device, comprising:
a first section, the first section including,
an outer cylindrical tube extending in a longitudinal direction,
an inner cylindrical tube within the outer cylindrical tube,
a liquid supply comprising a liquid material, the liquid supply contained in an outer annulus between the outer cylindrical tube and the inner cylindrical tube,
a heater located in the inner cylindrical tube,
a wick in communication with the liquid supply and in communication with the heater,
a mouth piece in fluid communication with the inner cylindrical tube at a proximal end of the first section, and
a male threaded connector at a distal end of the first section, the male threaded connector having first threads with a non-standard pitch; and
a second section, the second section including,
a power supply, and a female threaded connector at a proximal end of the second section, the female threaded connector having second threads mating with the non-standard pitch of the first threads, wherein a major diameter of the male and female threads is 7.00 mm and the non-standard pitch of the first and second threads is 0.6 mm, and the second threads have a root radius of 0.108 mm, a pitch diameter of 6.513 mm, a minor diameter of 6.188 mm, a thread height of 0.406 mm, and a tap drill diameter of 6.20 mm.

2. The e-vapor device of claim 1, wherein the first threads have a root radius of 0.108 mm, a pitch diameter of 6.513 mm, a minor diameter of 6.080 mm, a thread height of 0.460 mm, and a tap drill diameter of 6.20 mm.

3. An e-vapor device, comprising:
a section, the section including,
an outer cylindrical tube extending in a longitudinal direction,
an inner cylindrical tube within the outer cylindrical tube,
a liquid supply comprising a liquid material, the liquid supply contained in an outer annulus between the outer cylindrical tube and the inner cylindrical tube,
a heater located in the inner cylindrical tube,
a wick in communication with the liquid supply and in communication with the heater,
a mouth piece in fluid communication the inner cylindrical tube at a proximal end of the section, and
a male threaded connector at a distal end of the section, the male threaded connector having threads with a non-standard pitch,
wherein a major diameter of the threads is 7.00 mm and the non-standard pitch of the threads is 0.6 mm, and the threads have a root radius of 0.108 mm, a pitch diameter of 6.513 mm, a minor diameter of 6.080 mm, a thread height of 0.460 mm, and a tap drill diameter of 6.20 mm.

\* \* \* \* \*